United States Patent [19]

Duello

[11] Patent Number: 4,903,837
[45] Date of Patent: Feb. 27, 1990

[54] APPARATUS FOR DISPENSING AND ACCOUNTING ABSORBENT SURGICAL ARTICLES

[75] Inventor: Leonard E. Duello, Woodstock, Ga.

[73] Assignee: Kimberly-Clark Corporation, Neenah, Wis.

[21] Appl. No.: 232,724

[22] Filed: Aug. 16, 1988

[51] Int. Cl.[4] .............................................. B65D 83/00
[52] U.S. Cl. ..................................... 206/440; 206/233; 206/438; 206/494; 206/603
[58] Field of Search ............... 206/363, 370, 438, 603, 206/440, 494, 233, 812; 221/26, 27, 28, 30, 31; 116/278, 322, DIG. 14

[56] References Cited

U.S. PATENT DOCUMENTS

| | | | |
|---|---|---|---|
| 1,932,753 | 8/1933 | Ruegar et al. | 206/56 |
| 2,235,675 | 3/1941 | Fournier | 206/494 |
| 2,793,745 | 5/1957 | Cox | 206/56 |
| 3,061,087 | 10/1962 | Scrivens et al. | 206/63.2 |
| 3,104,012 | 9/1963 | Beamish | 206/46 |
| 3,258,156 | 6/1966 | Smith | 206/494 |
| 3,288,327 | 11/1966 | Cahlik | 221/70 |
| 3,338,400 | 8/1967 | Edgworth et al. | 206/63.2 |
| 3,481,462 | 12/1969 | Chapel | 206/63.2 |
| 3,630,202 | 12/1971 | Small | 128/296 |
| 3,749,237 | 7/1973 | Dorton | 206/57 |
| 3,770,119 | 11/1973 | Hultberg et al. | 206/63.2 |
| 3,826,406 | 7/1974 | Moniot | 221/58 |
| 3,893,566 | 7/1975 | Ross | 206/498 |
| 3,899,079 | 8/1975 | Seiter | 206/812 |
| 3,954,174 | 5/1976 | Kraus | 206/223 |
| 4,101,026 | 7/1978 | Bonk | 206/812 |
| 4,221,293 | 9/1980 | Anthony | 206/494 |
| 4,234,086 | 11/1980 | Dorton | 206/362 |
| 4,361,231 | 11/1982 | Patience | 206/362 |
| 4,418,821 | 12/1983 | Sandel | 206/370 |
| 4,735,317 | 4/1988 | Sussman et al. | 206/494 |
| 4,750,619 | 6/1988 | Cohen et al. | 206/363 |
| 4,770,320 | 9/1988 | Miles et al. | 206/494 |

FOREIGN PATENT DOCUMENTS

| | | | |
|---|---|---|---|
| 524328 | 12/1953 | Belgium | 206/440 |
| 803886 | 4/1951 | Fed. Rep. of Germany | 206/494 |
| 1027844 | 4/1958 | Fed. Rep. of Germany | 206/440 |
| 2409210 | 7/1979 | France | 206/440 |

*Primary Examiner*—Stephen Marcus
*Assistant Examiner*—Jes F. Pascua
*Attorney, Agent, or Firm*—Patrick C. Wilson

[57] ABSTRACT

A dispenser which may be sealed and sterilized, containing surgical absorbent pads for use during surgical operations, each surgical pad associated with an indicator strip rigidly affixed at one end to the inner wall of the dispenser such that removal of the absorbent pad extends the indicator strip to the exterior of the dispenser, the strip being of a length sufficient to prevent it inadvertent reintroduction into the dispenser, the spent absorbent pads reassociated with the exterior indicator strips to provide a visual positive accounting of absorbent pads used during the operation, the dispenser biased with a weighted flange extending from the bottom surface to land on a sterile field in a dispensing position when tossingly directed from a container towards the sterile field.

15 Claims, 2 Drawing Sheets

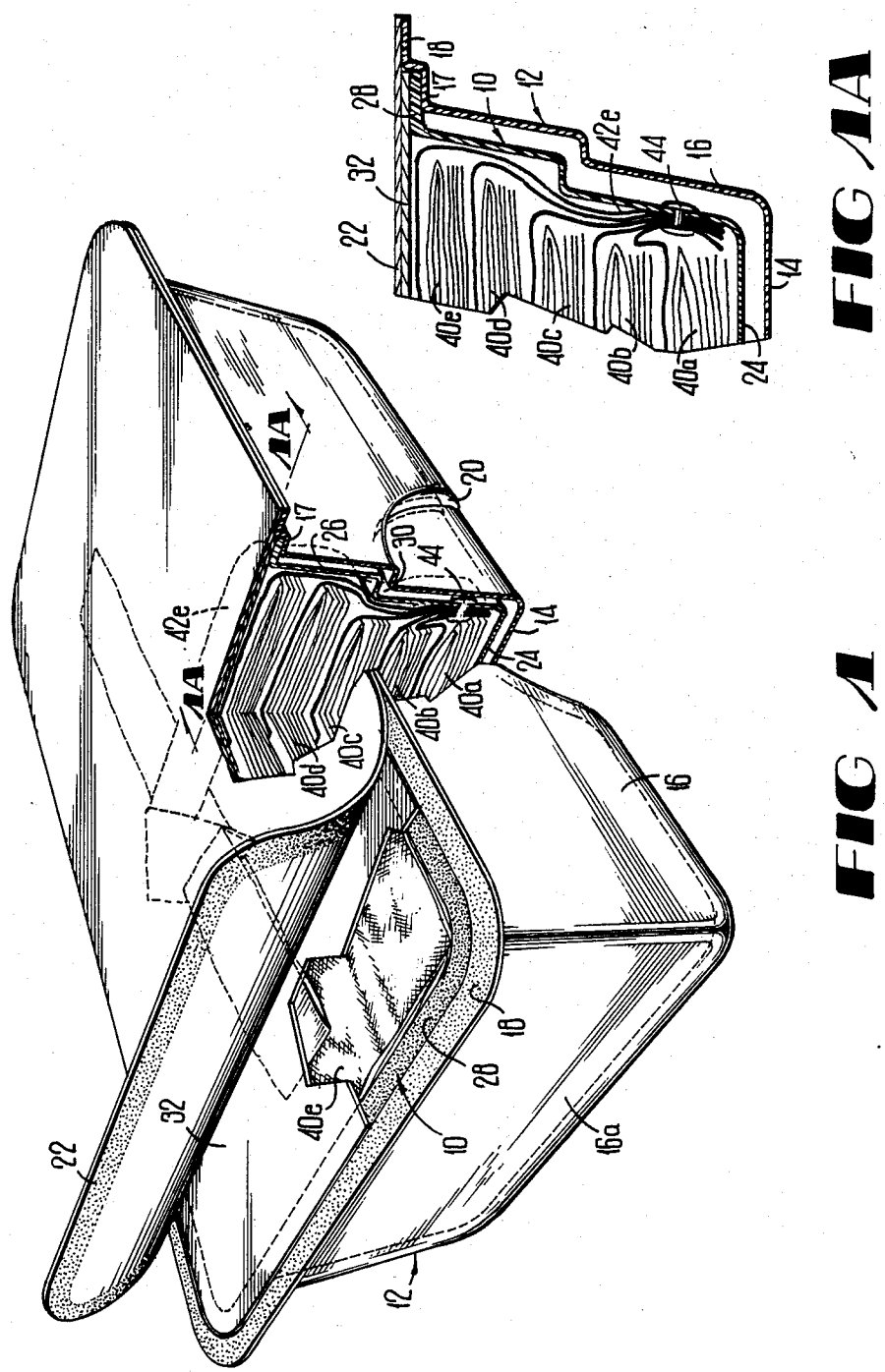

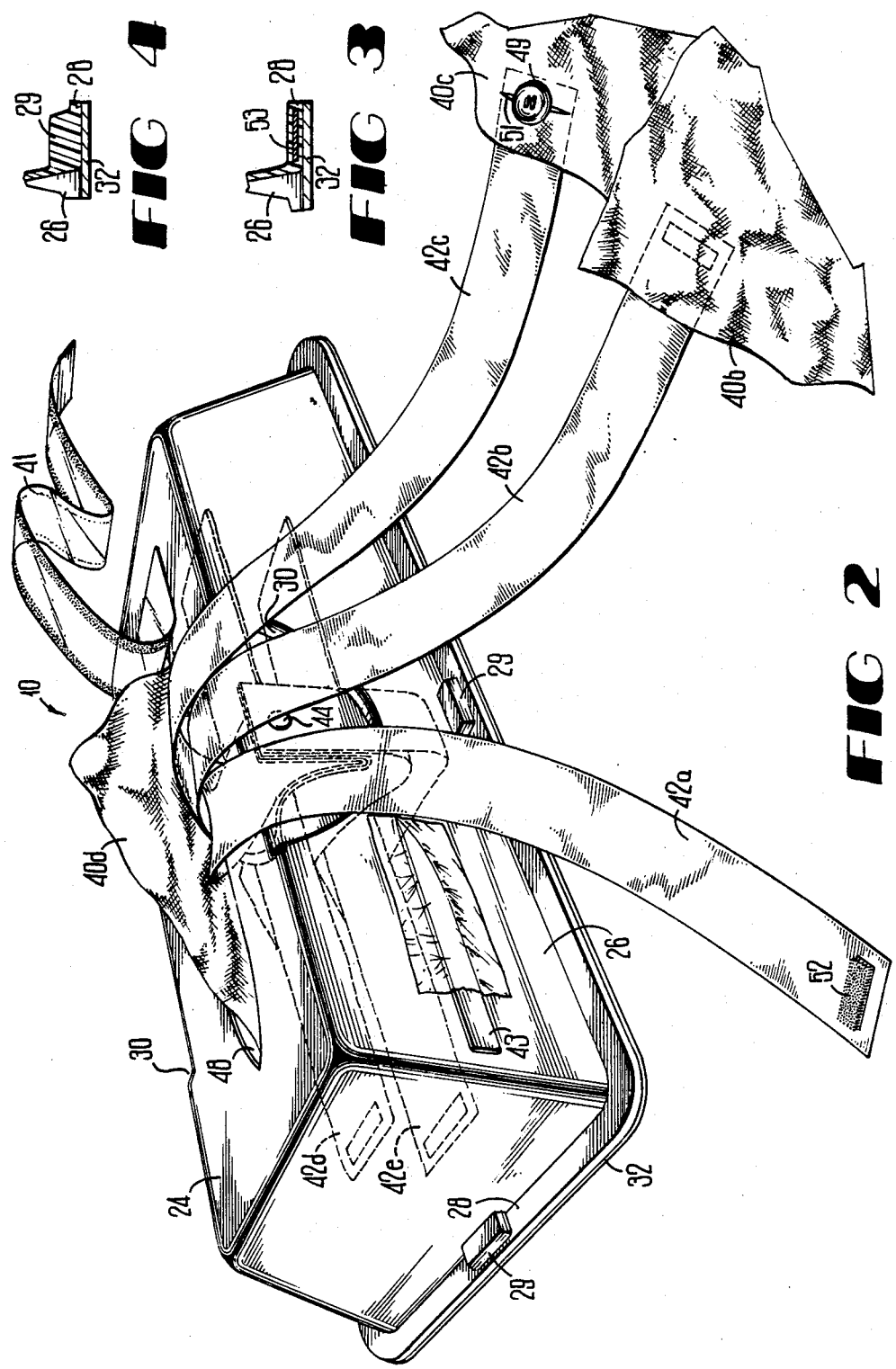

APPARATUS FOR DISPENSING AND ACCOUNTING ABSORBENT SURGICAL ARTICLES

TECHNICAL FIELD

The present invention relates to dispensers for surgical articles. More particularly, the present invention relates to a dispenser of absorbent surgical articles, which is biased to orientation in a dispensing position when tossed onto a sterile field of an operating room and which provides positive visual accounting of dispensed surgical articles.

BACKGROUND OF THE INVENTION

Typical operating room procedures followed in hospitals and other surgical areas establish rigid rules regarding sterile and non-sterile working areas, instruments, absorbent articles, and the like for use during an operation. These rules, coupled with other hospital procedures, provide a measure of assurance that only sterilized items or personnel may be used with or contact the patient during surgery. Typical operating rooms have sterile fields which include an operating table, supplies-and-instruments holding tables, and portions of various operating room personnel. Typically, the sterile supplies and instruments are placed in the operating room by a non-sterile person. The non-sterile person must place the supplies and instruments on the sterile field without touching or otherwise contaminating the sterilized items or the sterile field. Generally this involves handling the exterior surfaces of sterilized wrapping sheets or containers and tossing the contents through the air from a short distance away onto the sterile field.

Among the supplies typically used during a surgery are absorbent sponges, pads or the like. These generally are gauze or fabric-like woven materials made from cellulose and other materials which are subject to sterilization. A quantity of these absorbent materials are sealed in discardable containers and sterilized. Prior to use, the cover of the sterilized container may then be removed and the contents directed to the sterile field. There are a variety of known sterilizing techniques useful in preparing supplies and instruments for surgery, including exposure to ethylene oxide, steam, or radiation.

One known dispenser for absorbent surgical articles, such as bound laparotomy sponges, is the Kendall peel-tub sterilization container. This vacuum molded container may be inexpensively manufactured using a variety of plastics. A known number of sponges are rolled up, bundled together, and placed in the Kendall tub, and the tub and its contents are sterilized by a known approved technique prior to use of the contained sponges in an operation. Following the sterilization process, hospital rules consider the contents sterile and free from contamination while the tub exterior is considered non-sterile. That does not mean the exterior is contaminated; it means that there is no assurance that the exterior is free of contamination and thus the tub cannot be placed within the sterile field. Consequently, it is permissible for the exterior surface of the Kendall tub to be handled by a non-sterile technician setting up the operating room. The technician opens the container by peeling a cover away from the container and with a shaking motion, tosses the contents of the tub onto the sterile field. Sometimes the sponges or other contents of a sterilized container bounce off the sterile field onto the floor or other non-sterile area, which means these sponges or items cannot be used and thus are wasted.

The sterile pads placed on the sterile field are accounted and used by the medical personnel during the operation. After the operation, all absorbent articles (and instruments as well) must be accounted by physically counting each sponge used during the operation. The number of used sponges plus the number of sponges remaining available for use must equal the total number of sponges available prior to the operation. A known present practice to account the use of these absorbent articles requires manually counting the sponges when each sterilized container is opened by the technician and the sponges are placed on the sterile field. The count is repeated at the closing of each layer of the surgical area in the patient. Because the closing cannot proceed until each pad is accounted, tracking used pads is critical.

Although other techniques have been used previously, these have drawbacks or difficulties when used. One such method uses sponges with long attached tags. The tags remain outside the incision and aid in both counting and retrieval of the sponge. Such products however are little used because of the clutter introduced into the operative field by the many streamers coming from the patient's incision. Another known counting system includes a ring where sponges in the body are attached to the ring. When the ring is removed from the body area all sponges must be out of the body. Another known system attaches spent sponges to a rack with a fastener. Still another system employs a sheet having pouches which hold used sponges. These methods and structures to account for the number of absorbent articles removed from a dispenser have drawbacks. For instance, a pouch capable of holding five used sponges may by mistake hold fewer or more sponges than it was intended to hold. The contents of each pouch must be recounted until the total number of sponges is accounted. Also ribbons connected to the sponge clutter the incision area on the patient. Sponges interconnected on a common thread or wire may not be conveniently usable—moving a new sponge may dislodge another sponge already in place.

U.S. Pat. No. 1,932,753 issued to Rueger describes a package having a flexible strip which encircles or embraces individual cigarettes in a package. The strip is numbered adjacent its connection to each cigarette. Upon removal of a cigarette from the container, the number on the strip acts as a flag to indicate the number of cigarettes remaining in the container. The leading edge of the strip is severed from the strip and discarded as the cigarettes are removed from the pack.

U.S. Pat. No. 2,793,745 issued to Cox describes a package dispenser having a dome-shaped housing fastened to a backing panel. The housing may be scored or perforated to define an opening through which the contents of the package may be dispensed.

U.S. Pat. No. 3,338,400 issued to Edgworth et al. describes packing devices for articles requiring sterile and/or aseptic conditions. A flange dish includes a body portion with side walls and end walls for holding an article to be sterilized. A sheet member is bonded over the dish to establish a complete peripheral seal. Edgworth further describes including tear notches in the sheet member to facilitate rapid and convenient opening of the sealed package. Holding areas on the dish permit gripping the dish while avoiding contamination of the sterilized contents. Edgworth also suggests that the flange of the dish may extend axially to define an area for carrying legends or other identifiers or for including a perforated portion of the covering sheet to facilitate opening the package.

U.S. Pat. No. 3,481,462 issued to Chapel describes a disposable surgical article holder and counter. The holder provides an elongated base having a plurality of holes or openings in the upper surface. The base may be sealed with a removable cover. The surgical articles are replaced in the base openings after use, and a visual count can be made by determining whether any of the openings are unoccupied.

SUMMARY OF THE INVENTION

The present invention includes a plurality of sponges or other absorbent articles and accounting strips, which are collectively contained within a dispenser. Each sponge is associated with one accounting strip. One end of each accounting strip is rigidly fixed to an interior wall of the dispenser. Removal of an absorbent pad from the dispenser extends the accounting strip to the exterior of the dispenser. Spent absorbent pads may be reassociated with the exterior accounting strip to provide a visual positive accounting of absorbent pads used during the operation. The dispenser and its contents, all of which have to be sterilized, are housed within a protective outer peel pouch to permit handling by non-sterile personnel. The outer peel pouch is opened and the sterile dispenser and its contents directed to the sterile field by a tossing action which causes the dispenser to eject from the outer peel pouch. The outer peel pouch may then be discarded without compromising the sterility of the contents. Once the dispenser is on the sterile fields, both the dispenser and its contents may be handled and used as necessary during the course of the surgical procedure. Removal of the absorbent pad from the dispenser extends the accounting strip to the exterior of the dispenser. Each strip is of a length sufficient to prevent its inadvertent reintroduction into the dispenser and following the operation, spent absorbent pads may be reassociated with the accounting strips to provide a visual positive accounting of absorbent pads used.

The present invention permits accurate tracking of the sponges or absorbent articles removed from a dispenser. The dispenser of the present invention provides non-speculative accounting for the removed sponges before the patients' incision is closed. In another embodiment of the invention, the sponges may be reattached to the dispenser indicators and accounted as a unit by dispenser. For example, a dispenser having five indicator tabs extending from the dispenser is accounted by re-attaching a sponge to each indicator tab. A visual determination may then be made to establish that no dispenser has an external tab which is not associated with a spent sponge.

The present invention overcomes the limitations and disadvantages of dispensing absorbent surgical articles prior to an operation and counting the absorbent surgical articles after the operation. Absorbent surgical articles are retained within the dispenser until extracted for use. The dispenser is biased to land in a dispensing position and be stationary when tossed by the technician onto the sterile field of an operating room. Further, the dispenser of the present invention incorporates a counting aid into the dispenser.

The dispenser of the present invention contains a predetermined number of absorbent pads and associated indicator strips. One end of each indicator strip is rigidly attached to the dispenser while the distal end of the strip is associated with a sponge. When a sponge is removed from the dispenser, the indicator strip accompanies the sponge upon its removal. The strip is of a length sufficient to extend a relatively long distance out of the dispenser. This prevents the strip inadvertently reentering the dispenser. Operating room personnel can determine the number of sponges in use by counting the number of indicators outside of each dispenser used.

The dispenser of the present invention is biased to land on the sterile field in an upright dispensing position. The dispenser of the present invention also includes a number of surgical articles, and when tossed onto the sterile field, lands stationery. Use of such a dispenser reduces the opportunity for absorbent surgical articles to bounce off the sterile field and to fall to a non-sterile area of the operating room. The dispenser preferably incorporates a flange extending outwardly from the bottom edge of the dispenser to bias the dispenser to land in an upright dispensing position and to land stationery. Directional thrusting of the dispenser from its sterilization peel pouch directs the dispenser towards the sterile field with the flanged end down. Also, it is contemplated that weighting the flange relative to the other portions of the dispenser will bias the dispenser to land with the flange end downward even if tossed in a random manner at the sterile field. The flange, whether weighted or not, also enables a stationery landing such that the dispenser does not tend to move or continue travelling after first striking the sterile field.

The flanged dispenser is filled with a predetermined number of surgical absorbent pads and is placed within a sealable peel pouch. The flange of the dispenser is adjacent the edge opened by removing the peel-away cover. When placed in the peel pack, the top of the dispenser of the present invention is adjacent the bottom of the peel pack. In one embodiment of the present invention, the top of the dispenser contains an opening through which the absorbent surgical pads may be removed. In an alternate embodiment, the opening in the dispenser is sealably closed with a covering member. Perforations in the cover member permit the operating room personnel access to the contained sponges.

The technician when setting up the operating room obtains a sterilized package which includes the dispenser of the present invention. The technician grips the peel pack, removes the peel-away cover, and directionally tosses the dispenser from the peel pack towards the sterile field. Given a directional toss, the dispenser tends to land with its flanged base down. It is contemplated that the weighted base in an alternate embodiment biases the dispenser to land on its flanged base and to land stationery even when tossed in a random manner at the sterile field.

DESCRIPTION OF THE DRAWINGS

Objects and advantages of the present invention will become further apparent upon reading the following detailed description and upon reference to the following drawings, in which like elements have like identifiers.

FIG. 1 is a partially cut away perspective view of an absorbent surgical article dispenser according to the present invention.

FIG. 1A is a partial transverse cross-section of the dispenser illustrated in FIG. 1 taken along lines 1A—1A.

FIG. 2 is a perspective view of the dispensing apparatus of the present invention disposed on a sterile field illustrating the accounting use of the dispenser according to the present invention.

FIG. 3 is a cross-section view of the dispenser side wall, flange and bottom surface illustrating a metal strip embedded in the flange to weight the dispenser.

FIG. 4 is a cross-section of the dispenser side wall, flange and bottom surface illustrating a projection extending from the flange.

DETAILED DESCRIPTION OF THE PREFERRED EMBODIMENTS

The present invention provides a dispenser for a predetermined number of absorbent pads and associated indicator strips which visually account spent pads after a surgical operation. One end of each strip is rigidly fixed to the dispenser while the distal end of each strip is associated with one of the absorbent pads. When a pad is removed from the dispenser for use, the indicator strip accompanies the pad out of the dispenser and extends flexibly to the exterior of the dispenser. Sponges used during the operation may be accounted by reassociating each spent sponge with an exposed strip.

Turning first to FIG. 1, there is illustrated in cutaway perspective view an absorbent surgical article dispenser 10 according to the present invention. The dispenser 10 in a preferred embodiment is housed within an external container 12. In the illustrated embodiment of the present invention, both the dispenser 10 and the exterior container 12 are of a trapezoidal shape. The container 12 includes a base surface 14 integral with upward and outwardly extending sides 16. A two level rim extends around the container 12 at the upper distal end of the side walls 16. The rim includes a lower flange 17 and an upper flange 18, which extend laterally from the side of the container 12 and are parallel to the base 14. In the illustrated embodiment, a semicircular grip 20 is defined in the laterally opposite side surfaces 16 medial the end surfaces adjacent the bottom surface 14. A cover 22 detachably connected to the flange 18 defines the top surface parallel to the base 14. Glue or other adhesive on the flange 18 detachably secures the cover 22 to the container 12. The cover 22 in a preferred embodiment has a length and width greater than that of the base 14.

The dispenser 10 of the present invention preferably has a trapezoidal shape of a size permitting the dispenser 10 to nest within the container 12. As discussed above, the dispenser 10 of the present invention sits on the sterile field with its flanged surface down and is thus positioned in the container 12 upside down as illustrated. The dispenser 10 has a dispensing surface 24 integral with upward and outwardly tapering sides 26. At the upper distal end of the sides 26 is a flange 28. The flange 28 extends laterally from the sides 26 parallel to the surface 24 around the dispenser 10 to define a rim. In one embodiment, the flange 28 is weighted. The flange 28 of the illustrated embodiment is weighted, for example, by having a thickness greater than that of the sides 26. An alternate embodiment includes a metal strip in the flange while still another dispenser according to the present invention is injection molded and contains pockets into which the injected plastic pools to form weighted projections extending perpendicularly from the flange.

The illustrated embodiment includes a semicircular indentation 30 in the side 26, which matches the grip 20 of the container 12. A planar cover 32 connects with adhesive to the flange 28 to define a surface parallel to the surface 24 having a larger length and width than that of the surface 24. Held within the dispenser 10 is at least one absorbent pad 40 and an associated flexible ribbon 42. The illustrated embodiment includes five absorbent pads 40a—e and five associated flexible ribbons 42a–e. The indicator ribbons 42a–e may be colored to comply with hospital color codes or as appropriate to attract attention in the operating room. One end of each ribbon 42 is preferably rigidly secured to an interior surface of the dispenser.

FIG. 1A shows a transverse cross-section view of the embodiment of the present invention illustrated in FIG. 1. The rim of the container 12 includes the inner lower flange or ledge 17 on which the flange 28 of the dispenser 10 rests. The flange 28 is offset from the flange 18 to reduce the opportunity for gluing the dispenser 10 within the container 12 with the adhesive holding the cover 22 on the flange 18. Better illustrated in FIG. 1A is a button 44 which rigidly connects one end of each strip 42a–e to the dispenser 10. An alternate embodiment of the present invention has a single planar flange 18 extending laterally from the side 16 of the container 12. The dispenser 10 in that embodiment is sized to nest within the container 12 with the cover 32 displaced vertically from the cover 22 and the distal edge of the flange 28 adjacent the inner wall of the side 16.

FIG. 2 shows a perspective view of the dispenser 10 of the present invention disposed on a sterile field after being tossingly removed from the container 12. The flange 28 and cover 32 are downward and rest on the sterile field. A plurality of projections 29 used with an alternate embodiment extend from the flange 28. The surface 24 includes a longitudinally extending slot 48 through which may be dispensed the absorbent pads 40. An alternate embodiment includes as illustrated a detachable cover 41 and a knife 43. The cover 41 connects by an adhesive to the dispenser 10 and may be removed by a sterile member of the operating team after the non-sterile technician places the dispenser 10 on the sterile field. (Such a cover 41 further assures that the pads 40 remain sterile until just before the pads 40 in the dispenser 10 are needed for use). One end of each indicator pad 42 is adjacent and rigidly secured by the button 44 to the side 26 of the dispenser 10. The indicator strips 42 in an alternate embodiment are connected to the dispenser 10 by one of a variety of attachment technology such as sonic bonding, thermal bonding, hot melt adhesion, or a combination.

The distal end of each indicator strip 42 is associated with an absorbent pad 40. In a preferred embodiment, the distal end of each strip 42 includes a patch 52 of hook-type fabric such as VELCRO ™ fabric. The teeth on the patch 52 detachably engage the distal end of the ribbon 42b with an absorbent pad 40b. In an alternate embodiment also illustrated in FIG. 2 attachment of the indicator strip 42c to the dispensable sponge 40c is accomplished by a button 49 attached to the free end of the indicator strip 42 with a button hole 51 defined in one end of the sponge 40c. It is noted here that for clarity, FIG. 2 illustrates the ribbons 42d and 42e in hidden line and the associated pads 40d and 40e remain hidden in the dispenser 10. However, an exposed portion of the pad 40d is illustrated extending through the slot 48.

Referring now to FIG. 1, depending on the number of absorbent pads to be held within the dispenser 10, a group of ribbons 42 is gathered and aligned. One end of the group of ribbons 42 is rigidly secured by the button 44 to the side 26 of the container 10. An absorbent pad 40 is folded and associated with each ribbon 42. FIG. 2 illustrates an embodiment with each absorbent pad 40 detachably secured to the distal end of the ribbon 42 by the VELCRO TM patch 52 while another alternate illustrated embodiment includes the button 49 and button hole 51. Folded together, the pad 40 and its associated ribbon 42 are placed inside the dispenser 10. After the proper number of pads 40 and associated ribbons 42 are folded and placed within the dispenser 10, the cover 32 is rigidly glued to the exterior surface of the flange 28 to define a sealed surface which is to rest on a sterile site of an operating field.

The dispenser 10 is placed within a container 12 with the dispensing surface 24 down and the surface 32 up. The flanged surface 28 thus is adjacent the opening defined by the side wall 16 of the container 12 and the flange 28 rests on the ledge 17. A glue or other adhesive applied to the flange 18 seals the cover 22 on the flange 18 and the cover 22 closes the container 12.

The package of absorbent pads thus comprises a dispenser 10 containing the absorbent pads 40 and the associated accounting ribbons 42. The dispenser 10 in a preferred embodiment is sealably enclosed within an outer container 12 having a detachable cover 22. An alternate embodiment however wraps the dispenser 10 of the present invention in a cloth-like enclosure.

Prior to an operation, the entire package of the dispenser 10 and the container 12 is sterilized according to a medically acceptable technique such as exposure to ethylene oxide, high temperature steam, or radiation. A technician then sets up the operating room by placing the necessary instruments, equipment, and surgical supplies on the sterile field of the operating room. The sterilized package of absorbent pads is picked up by the technician. The exterior surface of the container 12 thereby becomes non-sterile because the container 12 is being handled by the non-sterile technician. The technician carefully unseals the container 12 by tearing the cover 22 away from the glued flange 18. This exposes the sterilized dispenser 10 of the present invention. The cover 22 is detached sufficiently from the container 12 to allow removal of the dispenser 10. Holding the container 12 by the sides 16, or in the illustrated embodiment by the grip 30, the technician stands a few feet away from the sterile field and shakes the container 12 to direct the dispenser 10 with a toss towards the sterile field. The dispenser 10 exits the container 12 and flies through the air to the sterile field. With the preferred directional toss, the dispenser 10 tends to land with its flanged surface 32 down. The flange 28 and surface 32 cooperate to assist the dispenser 10 in gripping the sterile field and becoming stationery with the surface 32 flat against the sterile field.

In a preferred embodiment, the flange 28 and cover 32 are weighted by having thicker walls than the sides 26 and surface 24. The weighted base in this alternate embodiment biases the dispenser 10 to land on its flanged base and remain stationery even when tossed in a random manner at the sterile field. An alternate embodiment illustrated in FIG. 3 molds a weight strip such as an elongated thin metal band 53 into the flange 28.

Another weighted embodiment illustrated in FIG. 4 provides the flange 28 with a plurality of projections 29 formed of pooled plastic injected into the dispenser mold during manufacture. The projections 29 are sized such that the volume of the projections holds enough plastic or other material to bias the dispenser to fall base down.

With the dispenser 10 properly placed with the surface 32 down against the sterile field, the surface 24 is upward and the slot 48 is accessible to a sterile member of the operating team. As needed, absorbent pads 40 may be extracted from the dispenser 10 through the slot 48. Removing the absorbent pad 40 pulls the flexible indicator strip 42 from the dispenser 10 through the slot 48. The indicator strip is of a length sufficient to extend a relatively long distance out of the dispenser 10. This prevents the strip 42 from inadvertently re-entering the dispenser 10. The absorbent pad 40 is detached from the patch 52 and used with the patient during the operation.

Following the operation, the operating room personnel can determine the number of sponges in use by counting the number of indicator strips 42 outside of each dispenser 10. To account for each spent sponge 40, the sponge 40 is removed from the patient and is re-attached to the patch 52 of a strip 42. As illustrated in FIG. 2, operating room personnel can quickly determine whether a sponge is unaccounted by determining whether a dispenser has an external indicator strip 42 (for example, strip 42a) which is not associated with a spent sponge.

Removal of the absorbent articles from the dispenser 10 is made by pulling the absorbent material through the container opening 48. As illustrated in the drawings, the trapezoidal container 10 has an opening in the smaller of the two parallel surfaces. For a dispenser of a regular rectangular shape the opening 48 preferably is placed on the flat parallel surface opposite the surface rimmed with the flange. It is contemplated that for other designs of the dispenser, the location of the opening would be on the uppermost point of the dispenser surface with the flat flanged dispenser surface considered the bottom.

In a preferred embodiment of the present invention, the opening 48 for removal of sponges is left uncovered. However, it is contemplated that the opening 48 may be covered in some fashion. FIG. 2 illustrates the detachable seal 41 which covers the opening 48. The seal 41 could be perforated for opening without an instrument or unperforated for opening with an instrument. The instrument such as the knife 43 shown in FIG. 2 may be included with the dispenser 10 by attaching it with tape or film to a side or otherwise contained between the dispenser 10 and the peel/pouch container 12 holding the dispenser 10. Such a cover and an opening instrument may be prepared from materials which would render both the cover and the instrument dimensionally and/or structurally stable during sterilization.

An alternate embodiment of the present invention may eliminate the exterior container 12. Such an embodiment would preferably include a cover for the opening 48 to assure that the sponges 40 enclosed in the dispenser 10 were sterile. The dispenser 10 may be placed in a sterile wrapper or blanket-type enclosure of types known in the industry, together with other instruments and supplies for sterilization treatment. Such a sterile wrapper would substitute for the container 12 of the present invention because it is important to provide an exterior gripping or contacting surface for the non-sterile technician to hold when placing the sterilized dispenser 10 with the adhesive pads on a sterile field of an operating room.

There are a variety of ways of placing the absorbent pads 40 and associated strips 42 within the dispenser 10. In one embodiment, each pad 40 and its associated strip 42 are folded together and placed in the dispenser 10. The pads 40 thus stack one on top of another. In another embodiment, each sponge 40 is rolled together with its associated strip 42. The rolled sponges 40 may then be placed in the dispenser 10 adjacent one another. Still another embodiment innerfolds the sponges 40 such that pulling the topmost sponge 40 from the dispenser 10 drags a portion of the next pad 40 so that, as illustrated in FIG. 2, a portion of the pad 40 extends through the slot 48 and is readily accessible by a member of the operating team. Thus the innerfolding releasably engages adjacent pads 40 with enough friction to pull the next pad 40 partially through the slot 48 when the upper adjacent pad 40 is fully removed with its associated strip 42 from the dispenser 10.

Many of the known types of absorbent pads include a fabric strip attached at its ends to a corner of the pad. The strip defines a flexible loop handle for pulling the pad from a dispenser, from a pile of pads, or from a patient during surgery. An alternate embodiment of the present invention for such types of absorbent pads rigidly connects both ends of each indicator strip 42 to the interior of the dispenser 10 to define a loop. Each loop-type strip is associated with an absorbent pad, and following the surgery, the spent pad may be connected by a knot to the indicator strip. The pad loop is pushed through the indicator loop and the pad is then pushed through the pad loop. Pulling the pad knots the two loops together and the spent pads may be visually accounted.

The sealable covers 22 and 32 of the container 12 and the dispenser 10 in a preferred embodiment are made from medical grade kraft paper. The covers 22 and 32 for closing the container 12 and dispenser 10 may be made of a woven or non-woven material of any appropriate substance which is structurally and/or dimensionally stable to sterilization procedures. Such closure materials are well known to those of skill in the art.

Although the present invention has been described with respect to a specific embodiment of the dispenser, other designs for the dispenser 10 may be successfully used with this invention as well. The dispenser 10 may be made of materials which render it dimensionally and/or structurally stable to sterilization, including such techniques as exposure to ethylene oxide, high temperature steam, or radiation. Such materials are well known to those in the art; because the pads 40 and the dispenser 10 are disposable, the dispenser 10 preferably is made of an inexpensive material. Vacuum forming the dispenser 10 with thermoplastic film is preferred, but the dispenser may readily be formed by injection molding techniques.

The dispenser 10 of the present invention illustrated in the drawings is trapezoidal in cross-section with a flange 28 extending outwardly from the distal edge of the walls 26 adjacent the larger of the two parallel surfaces. Other dispenser shapes include hemispherical, hemicylindrical, regular rectangular and other symmetrically shaped dispensers having a flange extending from the dispenser at the juncture of the sides and bottom. In the preferred embodiment, the flange is weighted to sustain the induced directional toss of the dispenser towards a landing area on the sterile field.

The principles, preferred embodiments and modes of operation of the present invention have been described in the foregoing specification. The invention is not to be construed as limited to the particular forms disclosed, since these are regarded as illustrative rather than restrictive. Moreover, variation and changes may be made by those skilled in the art without departing from the spirit of the invention as described by the following claims.

What is claimed is:

1. A dispenser for absorbent surgical sponges, comprising:
   a dispenser having an opening to its interior; and
   at least one elongated flexible strip rigidly secured at a first end to an interior surface of the dispenser and a distal end associated with an absorbent surgical pad sized to fit with the strip within the dispenser, the pad and the distal end of the strip having means for reassociating the pad with the strip.

2. A dispenser as recited in claim 1, further comprising a container having side and bottom walls and a removable seal to close an open end of the container, the container sized to house the dispenser.

3. A dispenser as recited in claim 1, wherein the distal end of the strip is detachably connected to the pad.

4. A dispenser as recited in claim 1, wherein the strip is of a length sufficient to permit substantially the entire length of the strip to be pulled outside the dispenser.

5. A dispenser as recited in claim 1, wherein the dispenser includes a substantially planar bottom surface.

6. A dispenser as recited in claim 5, wherein the bottom surface extends longitudinally and latitudinally beyond the sidewalls of the dispenser to define a flange.

7. A dispenser as recited in claim 6, wherein the thickness of the flange is greater than the thickness of the sidewalls.

8. A dispenser as recited in claim 1, further comprising a detachable seal to close the opening.

9. A dispenser as recited in claim 8, wherein the detachable seal is perforated.

10. A dispenser comprising:
    a container having a bottom surface;
    a flange extending around the perimeter of the bottom surface;
    a strip of metal embedded in the flange; and
    at least one elongated flexible strip rigidly secured at a first end to the interior surface of the dispenser an a distal end associated with an absorbent surgical pad sized to fit with the strip within the dispenser, the pad and the distal end of the strip having means for reassociating the pad with the strip.

11. A dispenser as recited in claim 10 wherein the strip is of a length sufficient to permit substantially the entire length of the strip to be pulled outside the dispenser.

12. A dispenser comprising:
    a container having a substantially planar bottom surface;
    a flange extending around the perimeter of the bottom surface;
    at least one projection extending from the flange; and
    at least one elongated flexible strip rigidly secured at a first end to an interior surface of the dispenser and a distal end associated with the absorbent surgical pad sized to fit with the strip within the dispenser, the pad and the distal end of the strip having means for reassociating the pad with the strip.

13. A dispenser as recited in claim 12, wherein the strip is of a length sufficient to permit substantially the entire length of the strip to be pulled outside the dispenser.

14. A dispenser for absorbent surgical sponges, comprising:
   a dispenser having an opening to its interior and a detachable seal to close the opening;
   an instrument attached to an exterior surface of the dispenser to sever the seal; and
   at least one elongated flexible strip rigidly secured at a first end to an interior surface of the dispenser and a distal end associated with an absorbent surgical pad sized to fit the strip within the dispenser.

15. A dispenser for absorbent surgical sponges, comprising:
   a dispenser having an opening to its interior; and
   at least one elongated flexible strip rigidly secured at a first end to an interior surface of the dispenser and a distal end associated with an absorbent surgical pad sized to fit with the strip within the dispenser, the pad further defining a button hole in one end of the pad and a button attached to the distal end of the strip, the button engaging the button hole of the pad to associate the pad and the strip.

* * * * *

UNITED STATES PATENT AND TRADEMARK OFFICE
CERTIFICATE OF CORRECTION

PATENT NO. : 4,903,837

DATED : February 27, 199-

INVENTOR(S) : Leonard E. Duello

It is certified that error appears in the above-identified patent and that said Letters Patent is hereby corrected as shown below:

In the Abstract, line 7 "it" should read -- its--;

Column 3, line 50 "patients" should read --patient's--;

Column 6, line 48, ")." should read --.)--; and

Column 10, line 48, Claim 12 "an a" should read --and a--.

Signed and Sealed this

Ninth Day of March, 1993

Attest:

STEPHEN G. KUNIN

*Attesting Officer*    *Acting Commissioner of Patents and Trademarks*